United States Patent [19]
Chikazawa

[11] Patent Number: 5,474,545
[45] Date of Patent: Dec. 12, 1995

[54] DIAPER AND/OR SANITARY NAPKIN

[76] Inventor: Osamu Chikazawa, 1-5-13, Nipponbashi, Chudo-Ku, Osaka, Japan

[21] Appl. No.: 987,358

[22] Filed: Dec. 7, 1992

[51] Int. Cl.⁶ ............................................. A61F 13/15
[52] U.S. Cl. ......................................... 604/368; 162/177
[58] Field of Search ................................ 604/358, 360, 604/385.1, 359, 368; 162/177

[56] References Cited

U.S. PATENT DOCUMENTS

| | | |
|---|---|---|
| Re. 32,957 | 6/1989 | Elias . |
| 2,179,591 | 11/1939 | Godchaux . |
| 3,034,922 | 5/1962 | Böe . |
| 3,344,789 | 10/1967 | Arnold et al. . |
| 3,442,819 | 5/1969 | Herbert . |
| 3,661,154 | 5/1972 | Torr . |
| 3,669,114 | 6/1972 | Morane . |
| 3,932,322 | 1/1976 | Duchane . |
| 3,935,363 | 1/1976 | Burkholder et al. . |
| 3,960,763 | 6/1976 | Lambou et al. . |
| 3,971,379 | 7/1976 | Chatterjee . |
| 3,983,053 | 9/1976 | Courtney et al. . |
| 4,206,718 | 6/1980 | Brewer . |
| 4,221,684 | 9/1980 | Antholz et al. . |
| 4,296,234 | 10/1981 | Mindt et al. . |
| 4,327,728 | 5/1982 | Elias . |
| 4,345,973 | 8/1982 | Ladisch et al. . |
| 4,381,782 | 5/1983 | Mazurak et al. . |
| 4,381,783 | 5/1983 | Elias . |
| 4,437,429 | 3/1984 | Goldstein et al. . |
| 4,444,149 | 4/1984 | Shomer . |
| 4,454,055 | 6/1984 | Richman et al. . |
| 4,460,642 | 7/1984 | Errede et al. . |
| 4,475,911 | 10/1984 | Gellert . |
| 4,500,670 | 2/1985 | McKinley et al. . |
| 4,525,410 | 6/1985 | Hagiwara et al. . |
| 4,699,620 | 10/1987 | Bernardin .............. 604/385.1 |
| 4,718,899 | 1/1988 | Itoh et al. . |
| 4,737,582 | 4/1988 | Goldman et al. . |
| 4,744,374 | 5/1988 | Deffeues .................. 604/360 |
| 4,783,239 | 11/1988 | Rich . |
| 4,822,349 | 4/1989 | Hursey et al. . |
| 4,826,497 | 5/1989 | Marcus et al. ............ 604/359 |
| 4,925,826 | 5/1990 | Hamm et al. . |
| 4,952,550 | 8/1990 | Wallach et al. . |
| 5,109,804 | 5/1992 | Chikazawa . |
| 5,151,091 | 9/1992 | Glang et al. ............ 604/385.1 |
| 5,175,046 | 12/1992 | Nguyen ................... 604/358 |

FOREIGN PATENT DOCUMENTS

| | | |
|---|---|---|
| 1015233 | 8/1977 | Canada . |
| 2451159 | 11/1980 | France . |
| 2627102 | 4/1987 | France . |

*Primary Examiner*—Randall L. Green
*Assistant Examiner*—Rob Clarke
*Attorney, Agent, or Firm*—Brumbaugh, Graves, Donohue & Raymond

[57] ABSTRACT

An absorbent article, such as a disposable diaper, sanitary napkin or tampon is disclosed, wherein the absorbent material comprises grains and the absorbent layer is biodegradable. The invention also discloses a process of making the absorbent article.

4 Claims, 1 Drawing Sheet

DIAPER AND/OR SANITARY NAPKIN

BACKGROUND OF THE INVENTION

The present invention relates to an absorbent article designed for absorbing aqueous solutions, more particularly physiological excretions and secretions. More particularly, this invention relates to an absorbent article having an absorbent inner layer comprising a coated expanded grain composition. The absorbent article comprises materials which have excellent absorbent properties and are biodegradable.

Disposal of soiled non-biodegradable diapers and catamenial devices, which give out offensive smells and harbor pathogenic organisms, contribute to environmental pollution. Further, disposal of these soiled items contribute to the accumulation of garbage. Landfills and other means of garbage disposal can no longer cope with the ever-increasing amounts of garbage that accumulate as the number of disposables used in our society grows. For these reasons, a non-biodegradable disposable product is undesirable if a biodegradable product having similar properties is available.

Accordingly, an object of this invention is to provide a disposable absorbent article comprising a superabsorbent material which is biodegradable, unlike the acrylate absorbent materials used in the prior art. It is a feature of this invention that the absorbent material is a coated expanded grain composition. It is another feature of this invention that the article is constructed as a first outer layer permeable to aqueous solutions, an absorbent inner layer, and a second outer layer, with the absorbent layer residing between the outer layers. Further, because the absorbent material dissolves easily, it will be carried away with ease if disposed of directly into a flush toilet or wastewater system.

Another object of this invention is to provide a method of making a disposable absorbent article using inexpensive materials, which can be mass-produced at low cost.

SUMMARY OF THE INVENTION

The present invention is directed to an absorbent article wherein the absorbent material is biodegradable and exhibits excellent absorbent properties for aqueous solutions. The absorbent article comprises a top outer layer permeable to aqueous solutions and a bottom outer layer and an absorbent layer between them, the absorbent layer comprising the steps of expanding grains and then coating the expanded grains with an inorganic powder material of zeolite in a range of 3–50 parts thereof for 100 parts of the grains, wherein the grains are pretreated by the steps of: (a) drying the grains, thereby reducing them in size; (b) adding water to the dried and size-reduced grains to obtain a paste; and (c) passing the paste through a fine sieve and heating the sifted paste at a temperature in the range of 120°–150°C. to transform the paste into a plurality of lumps having a diameter in the range of 1–2 millimeters.

The present invention is also directed to a process for making an absorbent article comprising the steps of: (a) providing a top outer layer, permeable to aqueous solutions; (b) providing an absorbent inner layer, the absorbent layer comprising the steps of heating grains and then coating the expanded grains with an inorganic powder material of zeolite in a range of 3–50 parts thereof for 100 parts of the grains, wherein the grains are pretreated by the steps, in the following sequence, of: (i) drying the grains, thereby reducing them in size; (ii) adding water to the dried and size reduced grains to obtain a paste; and (iii) passing the paste through a fine sieve and heating the sifted paste at a temperature in the range of 120°–150°C. to transform the paste into a plurality of lumps having a diameter in the range of 1–2 millimeters; (c) providing a bottom outer layer; and (d) securing the top and bottom layers to each other, wherein the absorbent article comprises a moisture-permeable top covering, an absorbent inner layer, and a bottom layer, the top and bottom layers being co-extensive and secured to one another at least on one side.

DETAILED DESCRIPTION OF THE PREFERRED EMBODIMENTS

The present invention relates to a disposable absorbent article comprising at least a first outer non-absorbent layer permeable to aqueous solutions, an absorbent layer, and at least a second outer layer. Preferably the second layer is impermeable to aqueous solutions. The present invention is especially suitable for the absorption of body fluids. An absorbent article in accordance with the invention may be in the form of a diaper, sanitary napkin or tampon, wherein the highly absorbent material used is biodegradable, and which, because it dissolves readily, can be disposed of directly into a flush toilet. The invention also relates to a process for producing such an article.

Figure 1:
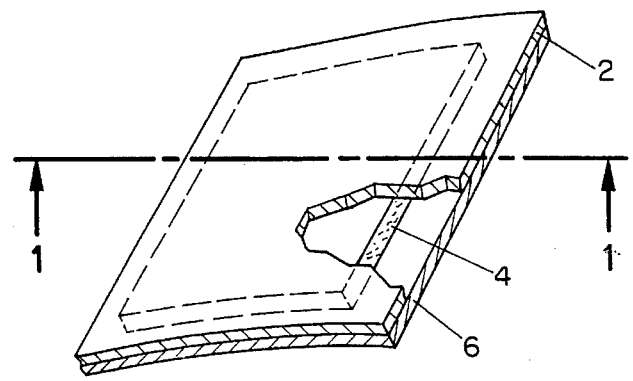
FIG. 1 is a perspective view of a diaper in accordance with the invention wherein the diaper is laid out flat, with a portion of the top layer removed to demonstrate the relationship between the various layers.
Figure 2:
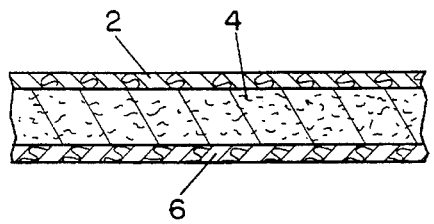
FIG. 2 is a cross-sectional view taken along line 1—1 of FIG. 1.

A diaper in accordance with the present invention is illustrated in FIG. 1, with a portion removed to illustrate the relationship of the layers. The diaper has a first outer facing layer 2 which is permeable to aqueous solutions and is in contact with the skin of the user, a second outer backing layer 6 which is impermeable to aqueous solutions and is disposed away from the user's skin. As illustrated in FIG. 2 which is a cross-sectional view taken along line 1—1 of FIG. 1, an absorbent layer 4 resides between layers 2 and 6. Absorbent layer 4 contains material which is highly absorbent and biodegradable. As depicted in FIG. 1, layers 2, 4 and 6 are rectangular, with layers 2 and 6 being the same size and coextensive with one another; however, other shapes and sizes may be employed in connection with the present invention. In this embodiment, absorbent layer 4 is smaller than layers 2 and 6 and is centrally disposed with respect to layers 2 and 6, whereby layers 2 and 6 extend beyond each of the four sides of layer 4 as shown in FIG. 1 in an amount sufficient to allow the edges to be less bulky than the rest of the diaper, thus allowing easy closure of the diaper. However, in other embodiments layers 2, 4 and 6 may be coextensive.

Figure 3:
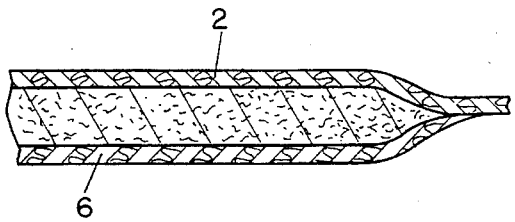
FIG. 3 is a cross-sectional view of a diaper in accordance with the invention wherein the first and second layers are secured to one another at least on one side.

As illustrated in FIG. 3 the first outer facing layer 2 and second outer backing layer 6 are secured to each other at least on one side. Both the facing and backing layer may consist of several layers. The facing and backing sheet materials suitable for use in this invention are any such materials that are well-known to those skilled in the art. Preferably, the facing sheet materials suitable for use in this invention can have fabric weight in the range of about 1 to 5 oz./yd.$^2$ and densities of less than 0.15 g./cc. generally in the range between 0.05 and 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness and drape characteristics in comparison to prior products incorporating any substantial amount of short fibers.

The facing sheet may also be made of an apertured, non-woven fabric as disclosed in U.S. Pat. Nos. 2,862,251; 3,081,514 and 3,081,515. Such fabrics are foraminous structures wherein groups or groupings of fibers have been rearranged from a fibrous nonwoven starting web into positions surrounding less dense fabric portions by passage of a fluid through the starting material.

The backing material imparts strength to the diaper as well as providing a moisture barrier. A plurality of glue lines are provided securing the bottom and top layers to each other around the edges as well securing the absorbent layer to the first and the second layers, and layer 4 to layers 2 and 6; alternatively, the first and second layers may be heat-sealed to one another. A suitable backing sheet material for a diaper in accordance with the present invention includes an opaque polyethylene web about 0.001 inch thick. Another suitable material for this purpose is a polyethylene terephthalate web having a thickness of about 0.005 inch.

Figure 4:
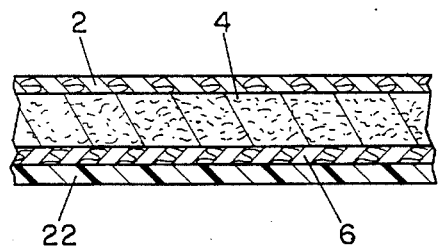
FIG. 4 is a cross-sectional view of a diaper, in accordance with the invention, wherein a layer impermeable to aqueous solutions is interposed between the absorbent layer and the second outer layer.

In an alternate embodiment, shown in FIG. 4, the second outer layer (22) is made of the same permeable material as the first outer layer (2), and an impermeable layer (6) is interposed between an absorbent layer (4) and the permeable second outer layer (22).

In accordance with the present invention, the absorbent layer is produced as described in U.S. Pat. No. 5,109,804 issued on May 5, 1992, or pending U.S. application Ser. No. 07/917,839, filed on Jul. 21, 1992. The absorbent layer comprises a highly absorbent material which is produced from cereals or grain seeds such as kaoliang, millet, wheat or rice or from plant materials comprising starch, preferably in large quantities such as tapioca, sweet potato, white potato and the like. All the above-mentioned starting materials used in the manufacture of the absorbent material of this invention, as used in this description and in the appended claims, are represented hereinafter by the term "grains". The grains may be pretreated by addition of moisture, size reduction, heating, and combinations thereof prior to heating, decompression and coating; as further discussed hereinbelow.

The grains are first subjected to a heat cooking and burst treatment, which comprises placing the grains in a pressure vessel and heating under tight seal so that water contained in the grains reaches a superheated state, and then decompressing or releasing the pressure rapidly to burst each grain granule to expanded or exploded form. In this invention, a lower grade of grains, for instance, wheat of a grade which cannot be applied to human service may be used.

Thereafter the burst grains are subjected to a stabilization or powdering step after air cooling, which comprises sprinkling or coating the grains with an inorganic alumina-silicate complex, namely zeolite, of which the general expression is given as $MeO.Al_2O_3.SiO_2.H_2O$), wherein Me is Na, K or Ca. The pellets are coated with the zeolite powder and subsequently dried. The zeolite coating increases the bulk density of the pellets by at least 10–20% percent. The aftertreatment as described above decreases the lumping tendency of the grains as well as the subsequent inconvenience in handling such highly bulky, fluffy granules. The described zeolite aftertreatment also increases the absorbance of water, and further, provides the absorbent material with the additional capacity to absorb offensive odors. Therein further, small amounts of one or more types of additives, such as agents for the enhancement of deodorization characteristics, colorants, antiseptics, medicaments, decay prevention agents and preservatives, can be introduced into the pellets in addition to the aforementioned zeolite powder.

In one preferred embodiment, the grains employed in the invention are obtained by causing lumps of tapioca or a 95:5 to 70:30 by weight tapioca-corn mixture to be initially heated under pressure in a humid atmosphere inside a grain cracking machine or other suitable means and kneaded together. The kneaded tapioca or tapioca-corn grains are then expelled under pressure through a nozzle of diameter 1 mm to 5 mm into the air and allowed to expand or puff at reduced pressure then cut with a cutter to form pellets. The tapioca or tapioca-corn grains may be pretreated by addition of moisture, size reduction, heating and combinations thereof prior to heating and expulsion under reduced pressure set forth hereinabove. The pellets, while their surfaces are still moist, are then introduced into a separate tank of additive such as an inorganic alumina-silicate powder for example, zeolite, as described above.

Figure 5:
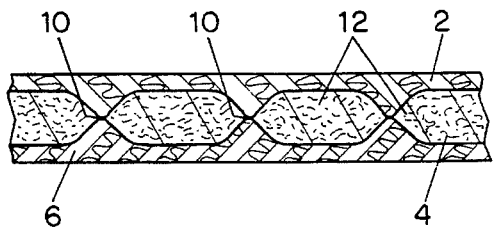
FIG. 5 is a cross-sectional view of a diaper in accordance with the invention wherein the absorbent layer has a plurality of pockets.

FIG. 5 illustrates an embodiment of the invention which has, in the absorbent layer 4, a plurality of pockets 12 separated form each other by glue lines 10, each pocket containing the absorbent material of the invention, the absorbent layer 4 residing between the permeable outer layer 2 and the impermeable outer layer 6.

Figure 6:
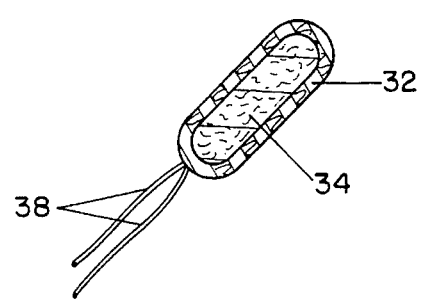
FIG. 6 is a perspective view of a tampon in accordance with the invention.

FIG. 6 illustrates a tampon which consists of an absorbent core 34 containing the absorbent material enveloped in a layer 32 that is permeable to aqueous solutions. Strings 38, necessary for removal of the tampon after use, are attached to the outer layer 32, although other removal means may be employed.

The actual design of the diaper, sanitary napkin and tampon can correspond to any convenient design well-known to those skilled in the art.

Although the invention addresses itself to diapers, sanitary napkins and tampons, the. present disclosure should be considered as being applicable to absorbent articles generally and is not intended to limit the invention to the embodiments discussed or illustrated.

I claim:

1. A process for making an absorbent article comprising the steps of:
    (a) providing a first outer layer which is permeable to aqueous solutions;
    (b) providing an absorbent inner layer, the absorbent layer comprising a zeolite-coated expanded grain composition prepared by the steps of heating grains and then coating the expanded grains with an inorganic powder material of zeolite in a range of 3–50 parts thereof for 100 parts of the grains, wherein the grains are pretreated by the steps, in the following sequence, of:

(i) drying the grains, thereby reducing them in size;
(ii) adding water to the dried and size reduced grains to obtain a paste; and
(iii) passing the paste through a fine sieve and heating the sifted paste at a temperature in the range of 120°–150°C. to transform the paste into a plurality of lumps having a diameter in the range of 1–2 millimeters;

(c) providing a second outer layer; and (d) securing the first and second layers to each other, with the absorbent layer residing therebetween, and the first and second layers are co-extensive and secured to one another at least on one side.

2. The process for making an absorbent article, as set forth in claim 1, wherein the grains of the absorbent layer are tapioca.

3. The process for making an absorbent article, as set forth in claim 1, wherein the grains of the absorbent layer are a mixture of tapioca and corn in a weight ratio of 95:5 to 70:30.

4. The process for making an absorbent article as set forth in claim 1, wherein the step of expanding the grain comprises heating the grains under pressure, expanding the grains into the atmosphere wherein the grains are puffed, and pelletizing the puffed grains.

* * * * *